United States Patent
Lee et al.

(10) Patent No.: US 11,337,906 B2
(45) Date of Patent: May 24, 2022

(54) HAIR CARE AND CONDITIONING COMPOSITIONS

(71) Applicant: L'OREAL, Paris (FR)

(72) Inventors: Heather Lee, Wayne, NJ (US); Dongcui Li, Metuchen, NJ (US); Jun Liang, Staten Island, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/731,654

(22) Filed: Dec. 31, 2019

(65) Prior Publication Data

US 2020/0206111 A1 Jul. 2, 2020

Related U.S. Application Data

(60) Provisional application No. 62/786,867, filed on Dec. 31, 2018.

(51) Int. Cl.
*A61K 8/34* (2006.01)
*A61Q 5/12* (2006.01)
*A61K 8/37* (2006.01)

(52) U.S. Cl.
CPC .............. *A61K 8/345* (2013.01); *A61K 8/34* (2013.01); *A61K 8/342* (2013.01); *A61K 8/37* (2013.01); *A61Q 5/12* (2013.01)

(58) Field of Classification Search
CPC . A61Q 5/12; A61K 2800/262; A61K 2800/31
See application file for complete search history.

(56) References Cited

U.S. PATENT DOCUMENTS

| | | |
|---|---|---|
| 4,859,456 A | 8/1989 | Marschner |
| 6,620,409 B2* | 9/2003 | Bossmann ............... A61K 8/37 424/401 |
| 6,645,480 B2 | 11/2003 | Giles |
| 8,563,016 B2 | 10/2013 | Agarelli et al. |
| 2002/0192173 A1* | 12/2002 | Glenn, Jr. ............... A61K 8/899 424/70.1 |
| 2006/0293197 A1* | 12/2006 | Uehara ................... A61K 8/02 510/122 |
| 2007/0071703 A1 | 3/2007 | Lin |
| 2008/0107616 A1 | 5/2008 | Hoffmann et al. |
| 2011/0135587 A1 | 6/2011 | Kinoshita et al. |
| 2011/0256083 A1 | 10/2011 | Smith, Jr. et al. |
| 2011/0268684 A1 | 11/2011 | Battermann et al. |
| 2014/0072523 A1 | 3/2014 | Battermann et al. |
| 2014/0196740 A1 | 7/2014 | Mette et al. |
| 2015/0150779 A1 | 6/2015 | Delowsky et al. |
| 2015/0174052 A1 | 6/2015 | Mette et al. |
| 2017/0216172 A1 | 8/2017 | Carballada et al. |
| 2018/0098923 A1 | 4/2018 | Hutton, III |

FOREIGN PATENT DOCUMENTS

| | | |
|---|---|---|
| EP | 2335671 A2 | 6/2011 |
| EP | 2335672 A2 | 6/2011 |
| EP | 2418002 A2 | 2/2012 |
| EP | 2594253 A2 | 5/2013 |
| JP | 2016117715 A | 6/2016 |
| KR | 20080010846 A | 1/2008 |
| KR | 2010 0081509 A | 7/2010 |
| KR | 20130046109 A | 5/2013 |
| WO | 03037280 A1 | 5/2003 |
| WO | WO 2003/037281 A1 | 5/2003 |
| WO | 2009074463 A2 | 6/2009 |
| WO | 2009074464 A2 | 6/2009 |
| WO | 2009074465 A2 | 6/2009 |
| WO | 2010082487 A1 | 7/2010 |
| WO | 2011054612 A2 | 5/2011 |
| WO | WO 2018/178341 A1 | 10/2018 |

OTHER PUBLICATIONS

International Search Report and Written Opinion dated Mar. 23, 2020 for corresponding PCT Application No. PCT/US2019/069102.

* cited by examiner

*Primary Examiner* — Robert A Wax
*Assistant Examiner* — William Craigo
(74) *Attorney, Agent, or Firm* — Polsinelli PC

(57) ABSTRACT

The present disclosure relates to hair care and conditioning compositions; and to methods for conditioning, managing, and/or styling the hair using the compositions. The hair conditioning and managing compositions are substantially anhydrous and include: propylene glycol; one or more monoalcohols having from 2 to 6 carbon atoms; one or more cationic surfactants; and one or more fatty compounds. The compositions are solubilized, non-emulsified compositions until applied to wet or damp hair, whereupon the compositions form a lamellar phase in situ.

16 Claims, 2 Drawing Sheets

HAIR CARE AND CONDITIONING COMPOSITIONS

CROSS-REFERENCE TO RELATED APPLICATIONS

This application claims the benefit under 35 U.S.C. § 119(e) of the filing date of U.S. Provisional Patent Application No. 62/786,867, filed on Dec. 31, 2018, entitled "HAIR CARE AND CONDITIONING COMPOSITIONS," the entirety of which is herein incorporated by reference.

FIELD OF THE DISCLOSURE

The present disclosure relates to hair care and conditioning compositions; and to methods for conditioning and styling the hair using the compositions.

BACKGROUND

Many individuals suffer from dry and damaged hair. Dryness and damage can occur due to several factors including weather exposure, mechanical treatments (e.g. brushing hair), excessive treatments using chemicals, dying hair, heat styling, etc. In combination, using cleansing products that can be excessively stripping of hair's natural oils, can also lead to split ends, dull hair, and exacerbate dry hair. To mitigate the damage, oil treatments, conditioner, hair masks, and chemical treatments are commonly used.

The popularity and usage of oils for dry hair treatments has increased due to their effectiveness and simplicity. Commonly used oils include olive oil, mineral oil, avocado oil, apricot kernel oil, rice bran oil, and coconut oil. However, one problem is that effects are not usually seen after more than several hours (e.g. 8 hours) of treatment and several treatments are usually required, making it time consuming and labor intensive.

Individuals desire a treatment for hair or damaged hair that is not time consuming and labor intensive to use. A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits.

However, there is still a need for providing improved hair manageability, for example, improved hair alignment, reduced unwanted volume (especially reduced frizz), and increased shine. There is also a need to develop hair care products that can impart other benefits at the same time in addition to caring and conditioning benefits, such as styling, volume, shaping, curl definition (for curly or wavy hair), and restylability or reshaping (without the need to reapply the product).

SUMMARY OF THE DISCLOSURE

The instant disclosure relates to hair care and conditioning compositions; and to methods for conditioning and styling the hair using the compositions. The compositions are transparent and substantially anhydrous. Upon application to wet or damp hair, the composition forms a lamellar phase, which surprisingly enhances the deposition of conditioning active agents such as cationic surfactants and fatty compounds onto the hair. The deposition of these conditioning active agents impart a smoothing and softening effect to the hair, resulting in the hair having a shiny and nourished appearance. The hair is easily detangled and dryness and fizziness are reduced or minimized. The compositions typically include:
  propylene glycol;
  one or more monoalcohols having from 2 to 6 carbon atoms;
    wherein the weight ratio of the propylene glycol to the monoalcohol(s) (propylene glycol:monoalcohol(s)) is from 20:1 to 1:1;
  one or more cationic surfactants;
  one or more fatty compounds;
  wherein the composition is a solubilized, non-emulsified composition until applied to the wet or damp hair, whereupon the composition forms a lamellar phase in situ.

The compositions can be applied immediately after shampooing the hair, for example, in place of a conditioner. The compositions can also be applied on hair immediately after shampooing and conditioning the hair, for example, as a mask rinse-off or leave-in treatment. The compositions can also be applied before shampooing the hair as pre-treatment compositions. Moreover, the compositions are applied to wet or damp hair and massaged into the hair to ensure uniform coverage. After application to the hair, the hair may be rinsed with water, dried, and styled as desired. Another unique aspect of the compositions is that they may be used as a leave-on product. The compositions can be applied to wet or damp hair and allowed to remain on the hair indefinitely, i.e., the hair composition is not removed or rinsed from the hair prior to styling the hair.

BRIEF DESCRIPTION OF THE DRAWING

Implementation of the present technology will now be described, by way of example only, with reference to the attached figures, wherein.

Figure 1:
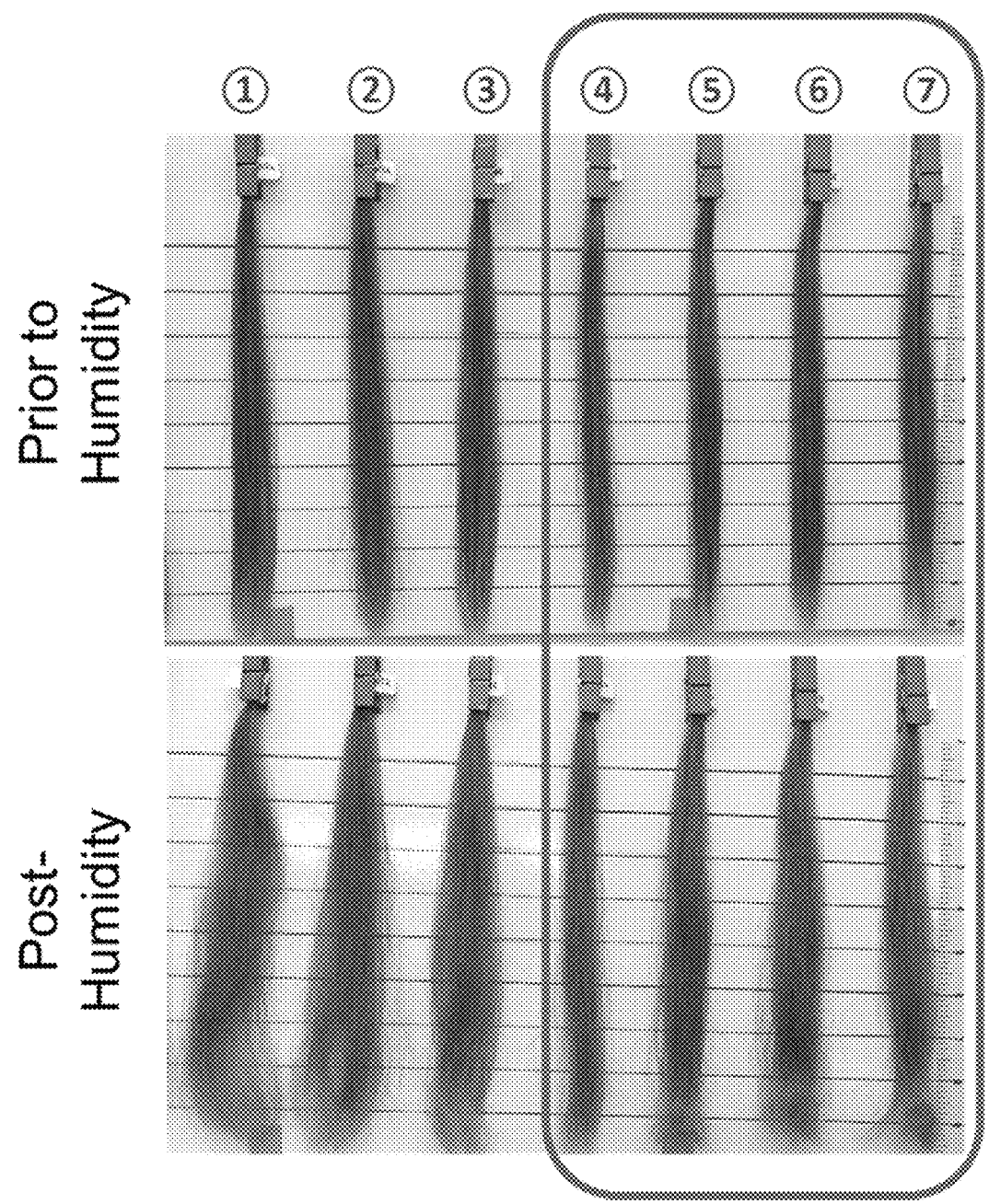
FIG. 1 includes pictures of hair swatches treated with compositions according to the instant disclosure and subjected to humidity.

It should be understood that the various aspects are not limited to the arrangements and instrumentality shown in the drawings.

DETAILED DESCRIPTION OF THE DISCLOSURE

The present disclosure relates to a transparent and substantially anhydrous cosmetic composition comprising:
  about 20 to about 95 wt. % of propylene glycol;
  about 5 to about 70 wt. % of one or more monoalcohols having from 2 to 6 carbon atoms;
  wherein the weight ratio of the propylene glycol to the monoalcohol(s) (propylene glycol:monoalcohol(s)) is from 20:1 to 1:1;
    about 0.1 to about 5 wt. % of one or more cationic surfactants; and
    about 0.1 to about 20 wt. % of one or more fatty compounds;
    wherein the composition is a solubilized, non-emulsified composition until applied to the wet or damp hair, whereupon the composition forms a lamellar phase in situ; and all percentages by weight are based on the total weight of the composition.

The term "transparent" with respect to a transparent composition indicates that the composition has transmittance of at least 80% at a wavelength of 600 nm, for example measured using a Lambda 40 UV-visible spectrometer. The compositions may have, for example, a transmittance of at least 80%, at least 90%, or at least 95% at a wavelength of 600 nm, measured, for example, using a Lambda 40 UV-visible spectrometer. The term "clear" is interchangeable with the term "transparent" for purposes of the instant disclosure.

The compositions are essentially anhydrous. The phrase "essentially anhydrous" is interchangeable with the phrase "essentially free of water" or "substantially free of water." An essentially anhydrous composition may include up to 5 wt. % of water regardless of whether the water is added to the composition or part of a raw material. Nonetheless, the essentially anhydrous composition may include less than 4 wt. %, less than 3 wt. %, less than 2 wt. %, less than 1 wt. %, or less than 0.5 wt. % of water.

The compositions of the instant disclosure typically have a viscosity of about 10 mPa·s to about 10,000 mPa·s at 25° C. The viscosity measurements can be carried out, for example, using a Broooksfield viscometer, Model RVT (Brookfield Engineering Laboratories, Inc.) at about 20 revolutions per minute (RPM), at ambient room temperature of about 20 to 25° C.; spindle sizes may be selected in accordance with the standard operating recommendations form the manufacturer, ranging from disk spindle No. 1 to No. 4.

The compositions of the instant disclosure include propylene glycol (propane-1,2-diol). Propylene glycol was found to be particularly advantageous because it provides greater deposition of the conditioning active ingredients (e.g., cationic surfactants and fatty compounds) than other glycols. The total amount of propylene glycol can vary but is typically about 20 to about 95 wt. % of propylene glycol, based on the total weight of the composition. In some instances, the total amount of propylene glycol is about 30 to about 90 wt. %, about 40 to about 90 wt. %, or about 50 to about 90 wt. %, including ranges and sub-ranges therebetween. Similarly, is some cases, the total amount of propylene glycol may be about 20 to about 80 wt. %, about 30 to about 80 wt. %, about 40 to about 80 wt. %, or about 50 to about 80 wt. %, including ranges and sub-ranges therebetween, based on the total weight of the composition.

In addition to the propylene glycol, the compositions of the instant disclosure may optionally include additional glycols, for example, one or more glycols selected from ethylene glycol, butylene glycol, hexylene glycol, pentylene glycol, diethylene glycol, dipropylene glycol, 1,3 propanediol, and glycerin.

The total amount of additional glycols (glycols other than propylene glycol) can vary but in some instances is from about 0.1 to about 50 wt. %, based on the total weight of the composition. In some cases, the total amount of additional glycols (glycols other than propylene glycol), may be about 0.1 to about 40 wt. %, about 0.1 to about 30 wt. %, about 0.1 to about 20 wt. %, about 0.1 to about 10 wt. %, about 1 to about 50 wt. %, about 1 to about 40 wt. %, about 1 to about 30 wt. %, about 1 to about 20 wt. %, or about 1 to about 10 wt. %, including ranges and sub-ranges therebetween based on the total weight of the composition.

In some instances, the compositions of the instant disclosure include butylene glycol but other instances, the compositions are free or essentially free of butylene glycol. If present, the total amount of butylene glycol can vary but is typically from about 0.1 to about 50 wt. %, based on the total weight of the composition. In some cases, the total amount of butylene glcyol may be about 0.1 to about 40 wt. %, about 0.1 to about 30 wt. %, about 0.1 to about 20 wt. %, about 0.1 to about 10 wt. %, about 1 to about 50 wt. %, about 1 to about 40 wt. %, about 1 to about 30 wt. %, about 1 to about 20 wt. %, or about 1 to about 10 wt. %, including ranges and sub-ranges therebetween based on the total weight of the composition.

The compositions include one or more monoalcohols having from 2 to 6 carbon atoms. For example, the one or more monoalcohols may be selected from ethanol, propanol, butanol, pentanol, hexanol, isopropyl alcohol, cycohexanol, isobutyl alcohol, 2-methyl-2-butanol (2-methylbutan-2-ol), and a mixture thereof.

The total amount of monoalcohols can vary but is typically from about 5 to about 70 wt. %, based on the total weight of the composition. In some instances, the total amount of monoalcohols is from about 5 to about 60 wt. %, about 5 to about 50 wt. %, about 5 to about 45 wt. %, about 5 to 40 wt. %, about 5 to 35 wt. %, about 5 to about 30 wt. %, about 10 to about 70 wt. %, about 10 to about 60 wt. %, about 10 to about 50 wt. %, about 10 to about 45 wt. %, about 10 to about 40 wt. %, about 10 to about 35 wt. %, or about 10 to about 30 wt. %, including ranges and sub-ranges therebetween based on the total weight of the composition.

In some instances, the one or more monoalcohols include ethanol. For example, the compositions may include ethanol and optionally one or more additional monoalcohols having from 2 to 6 carbon atoms. The total amount of ethanol may vary but it typically from about 5 to about 60 wt. %, based on the total weight of the composition. In some instances, the total amount of ethanol is from about 5 to about 50 wt. %, about 5 to about 45 wt. %, about 5 to about 40 wt. %, about 5 to 35 wt. %, about 5 to about 30 wt. %, about 10 to about 70 wt. %, about 10 to about 60 wt. %, about 10 to about 50 wt. %, about 10 to about 45 wt. %, about 10 to about 40 wt. %, about 10 to about 35 wt. %, or about 10 to about 30 wt. %, including ranges and sub-ranges therebetween, based on the total weight of the composition.

The total amount of propylene glycol is typically at least the same or higher than the total amount of the monoalcohol(s) having from 2 to 6 carbon atoms in the compositions. Often, the compositions include more propylene glycol than monoalcohol(s) having from 2 to 6 carbon atoms, i.e., a higher weight percent of the composition is propylene glycol than monoalcohols having from 2 to 6 carbon atoms. The ratio of propylene glycol to the total amount of monoalcohol(s) having from 2 to 6 carbon atoms (propylene glycol:monoalcohol(s)) may be from 20:1 to 1:1. In some instances, the ratio is from 20:1 to 1.1:1, 20:1 to 1.5:1, or 20:1 to 2:1, including ranges and sub-ranges therebetween. Similarly, in some instances, the ratio is from 18:1 to 1:1, 18:1 to 1.1:1, 18:1 to 1.5 to 1, 18:1 to 2:1, including ranges and sub-ranges therebetween.

The term "cationic surfactant" means a surfactant that may be positively charged when it is contained in the compositions according to the disclosure. This surfactant may bear one or more positive permanent charges or may contain one or more functional groups that are cationizable in the composition according to the disclosure. Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In some instances, the cationic surfactant is preferably selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof.

In some instances, the cationic surfactants are more preferably selected from cetrimonium chloride, behentrimonium chloride, behentrimonium methosulfate, stearamidopropyl dimethylamine, and a mixture thereof.

Moreover, in some cases, the cationic surfactant is most preferably cetrimonium chloride, behentrimonium chloride, or a mixture thereof.

A more exhaustive list of cationic surfactants that may be included in the hair-treatment compositions is provided later, under the heading "Cationic Surfactants."

The total amount of cationic surfactant(s) in the composition can vary but is typically from about 0.1 to about 5 wt. %, based on the total weight of the composition. In some cases, the total amount of cationic surfactant(s) is from about 0.1 to about 4 wt. %, about 0.1 to about 3 wt. %, about 0.1 to about 2 wt. %, about 0.5 to about 5 wt. %, about 0.5 to about 4 wt. %, about 0.5 to about 3 wt. %, or about 0.5 to about 2 wt. %, including ranges and sub-ranges therebetween, based on the total weight of the composition.

Non-limiting examples of fatty compounds include fatty esters, fatty alcohols, glyceryl esters (glycerol esters), fatty acids, fatty esters, alkyl ethers of fatty alcohols, fatty acid esters of fatty alcohols, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof. Non-limiting examples of fatty esters include fatty carbonate esters, glycerol fatty esters, sucrose fatty esters, sorbitan fatty ester, fatty acid esters, or mixtures thereof. Non-limiting examples of the fatty alcohols, fatty acids, fatty alcohol derivatives, and fatty acid derivatives are found in International Cosmetic Ingredient Dictionary, Sixteenth Edition, 2016, which are incorporated by reference herein in its entirety. A more exhaustive but non-limiting list of useful fatty compounds is provided later, under the heading "fatty compounds."

The total amount of fatty compounds in the compositions may vary but is typically from about 0.1 to about 20 wt. %, based on the total weight of the composition. The total amount of fatty compounds may be from about 0.1 to about 15 wt. %, about 0.1 to about 10 wt. %, about 0.1 to about 8 wt. %, about 0.1 to about 5 wt. %, about 0.5 to about 20 wt. %, about 0.5 to about 15 wt. %, about 0.5 to about 10 wt. %, about 0.5 to about 8 wt. %, about 0.5 to 5 wt. %, about 1 to about 20 wt. %, about to about 15 wt. %, about 1 to about 10 wt. %, about 1 to about 8 wt. %, or about 1 to about 5 wt. %, including ranges and sub-ranges therebetween, based on the total weight of the composition.

In some instances, the compositions of the instant disclosure include one or more fatty esters, i.e., one or more of the fatty compound(s) is a fatty ester. Non-limiting examples of fatty esters include fatty carbonate esters (in particular dialkyl carbonates), glycerol fatty esters, sucrose fatty esters, sorbitan fatty ester, fatty acid esters, or mixtures thereof. Additional non-limiting examples of fatty esters that may be used include fatty esters such as esters of $C_{6-22}$ fatty acids with a monohydric alcohol and/or esters of $C_{6-22}$ fatty alcohols with a monocarboxylic acid. More specific non-limiting examples include isopropyl isostearate, n-propyl myristate, isopropyl myristate, hexyl laurate, hexadecyl isostearate, hexydecyl laurate, hexyldecyl octanoate, n-propyl palmitate, isopropyl palmitate, and mixtures thereof.

Preferable fatty esters include fatty carbonate esters (also referred to as "fatty carbonates"). Fatty carbonates include dialkyl carbonates. Non-limiting examples of dialkyl carbonates include those of the following formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, for example, C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof. In some instances, it is preferable to include one or more dialkyl carbonates, in particular dicaprylyl carbonate.

In some cases, the one or more fatty esters is a glycerol ester of fatty acids or glyceryl esters (or glycerol fatty esters), for example, glyceryl monomyristate, glyceryl monopalmitate, glyceryl monostearate, glyceryl isostearate, glyceryl monooleate, glyceryl dioleate, glyceryl distearate, glyceryl laurate, trilaurin, triarachidin, tribehenin, tricaprin, tricaprylin, caprylic/capric triglyceride, trierucin, triheptanoin, triheptylundecanoin, triisononanoin, triisopalmitin, triisostearin, trilinolein, trimyristin, trioctanoin, triolein, tripalmitin, tripalmitolein, triricinolein, tristearin, triundecanoin, and mixtures thereof.

Additional, non-limiting examples of fatty esters include diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palm itate, 2-ethylhexyl palm itate, 2-hexyldecyl palm itate, 2-heptylundecyl palm itate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, diisostearyl malate, dicaprylyl carbonate, and mixtures thereof.

The total amount of the fatty ester(s) in the composition, if present, may vary but is typically from about 0.1 to about 15 wt. %, based on the total weight of the composition. In some instances, the total amount of fatty ester(s) is from about 0.1 to about 12 wt. %, about 0.1 to about 10 wt. %, about 0.1 to about 8 wt. %, about 0.1 to about 5 wt. %, about 0.5 to about 15 wt. %, about 0.5 to about 12 wt. %, about 0.5 to about 10 wt. %, about 0.5 to about 8 wt. %, or about 0.5 to about 5 wt. %, based on the total weight of the composition.

In some instances, the compositions of the instant disclosure include one or more fatty alcohols, i.e., one or more of the fatty compound(s) is a fatty alcohol. The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In some instances, the compositions include at least one solid fatty alcohol. It is preferable that the solid fatty alcohols are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more more preferably 14 to 22 carbon atoms.

In particular, it is possible to mention, alone or as a mixture: lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); ligno-ceryl alcohol (1-tetracosanol); ceryl alcohol (1-hexacosa-nol); montanyl alcohol (1-octacosanol); myricylic alcohol (1-triacontanol).

Preferably, the solid fatty alcohol is chosen from myristyl alcohol, cetyl alcohol, stearyl alcohol, myristyl alcohol, behenyl alcohol and mixtures thereof such as cetylstearyl or cetearyl alcohol.

In an embodiment, the solid fatty alcohol is chosen from myristyl alcohol.

The liquid fatty alcohols, in particular those containing C10-C34, preferably have branched carbon chains and/or have one or more, preferably 1 to 3 double bonds. They are preferably branched and/or unsaturated (C=C double bond), and contain from 12 to 40 carbon atoms.

The liquid fatty alcohols may be represented by: R—OH, wherein R denotes a C12-C24 branched or straight alkyl group or an alkenyl group, R being optionally substituted by one or more hydroxy groups. Preferably, the liquid fatty alcohol is a branched saturated alcohol. Preferably, R does not contain a hydroxyl group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

In some instances, the compositions include one or more fatty alcohols selected from decyl alcohol, undecyl alcohol, dodecyl alcohol, myristyl alcohol, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the compositions preferably include myristyl alcohol.

The total amount of the fatty alcohols in the composition, if present, may vary but is typically from about 0.1 to about 15 wt. %, based on the total weight of the composition. In some instances, the total amount of fatty alcohols is from about 0.1 to about 12 wt. %, about 0.1 to about 10 wt. %, about 0.1 to about 8 wt. %, about 0.1 to about 5 wt. %, about 0.5 to about 15 wt. %, about 0.5 to about 12 wt. %, about 0.5 to about 10 wt. %, about 0.5 to about 8 wt. %, or about 0.5 to about 5 wt. %, including ranges and sub-ranges therebetween, based on the total weight of the composition.

In some instances, the compositions of the instant disclosure include at least one fatty ester and at least one fatty alcohol.

In some instances, the compositions of the instant disclosure include at least one glycerol fatty ester and at least one fatty alcohol.

In some instances, the compositions of the instant disclosure include at least one fatty ester, at least one glycerol fatty ester, and at least one fatty alcohol.

In some instances, the fatty ester is a fatty carbonate ester (also referred to as "fatty carbonate"). Accordingly, the compositions may include at least one fatty carbonate, in particular at least one dialkyl carbonate, and at least one fatty alcohol. For example, the composition may include at least one dialkyl carbonate selected from C14-15 dialkyl carbonate, dicaprylyl carbonate, diethyl carbonate, dihexyl carbonate, diethylhexyl carbonate, dimethoxyphenyl phenyloxyethyl ethylcarbonate, dimethyl carbonate, dipropyl carbonate, dipropylheptyl carbonate, dioctyl carbonate, and a mixture thereof; and at least one fatty alcohol selected from decyl alcohol, undecyl alcohol, dodecyl alcohol, myristyl alcohol, cetyl alcohol, stearyl alcohol, isostearyl alcohol, isocetyl alcohol, behenyl alcohol, linalool, and oleyl alcohol. In some cases, the compositions include a combination of dicaprylyl carbonate and myristyl alcohol.

In some cases, the at least one glycerol fatty ester is selected from glyceryl monomyristate, glyceryl monopalmitate, glyceryl monostearate, glyceryl isostearate, glyceryl monooleate, glyceryl dioleate, glyceryl distearate, glyceryl laurate, trilaurin, triarachidin, tribehenin, tricaprin, tricaprylin, caprylic/capric triglyceride, trierucin, triheptanoin, triheptylundecanoin, triisononanoin, triisopalmitin, triisostearin, trilinolein, trimyristin, trioctanoin, triolein, tripalmitin, tripalmitolein, triricinolein, tristearin, triundecanoin, and mixtures thereof. In some cases, the compositions include a combination of caprylic/capric triglyceride and myristyl alcohol.

In some cases, the compositions include a combination of dicaprylyl carbonate, caprylic/capric triglyceride and myristyl alcohol.

One or more thickening agents can optionally be included in the compositions of the instant disclosure. Thickening agents may be referred to as "thickeners" or "viscosity modifying agents." Thickening agents are typically included to increase the viscosity of the compositions. Nonetheless, in some instances, certain thickening agents provide additional, surprising benefits to the compositions. Non-limiting examples of thickening agents include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof. Particular types of thickening agents that may be mentioned include the following:

a. Carboxylic acid or carboxylate based homopolymer or co-polymer, which can be linear or crosslinked: These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLY-GEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickeners useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

b. Polyquaternium Compounds: Non-limiting examples, include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

c. Celluloses: Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

d. Polyvinylpyrrolidone (PVP) and co-polymers: Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

e. Sucrose esters: Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

f. Polyglyceryl esters: Non-limiting polyglycerol esters of fatty acids (polygylceryl esters) include those of the following formula:

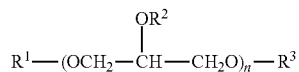

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

g. C8-24 hydroxyl substituted aliphatic acid and C8-24 conjugated aliphatic acid: Non-limiting examples include conjugated linoleic acid, cis-parinaric acid, trans-7-octadecenoic acid, cis-5,8,11,14,17-eicosapentanoic acid, cis-4,7,10,13,16,19-docosahexenoic acid, columbinic acid, linolenelaidic acid, ricinolaidic acid, stearidonic acid, 2-hydroxystearic acid, alpha-linolenic acid, arachidonic acid, cis-11,14-eicosadienoic acid, linolelaidic acid, monopetroselinic acid, petroselinic acid, ricinoleic acid, trans-vaccenic acid, cis-11,14,17-eicosatrienoic acid, cis-5-eicosenoic acid, cis-8,11,14-eicosatrienoic acid, hexadecatrienoic acid, palmitoleic acid, petroselaidic acid, trans trans farnesol, cis-13,16-docosadienoic acid, cis-vaccenic acid, cis-11-eicosenoic acid, cis-13,16,19-docosatrienoic acid, cis-13-octadecenoic acid, cis-15-octadecanoic acid, cis-7,10,13,16 docosatetraenoic acid, elaidic acid, gamma-linolenic acid, geranic acid, geranyl geranoic acid, linoleic acid, oleic acid, pinolenic acid, trans-13-octadecenoic acid. More preferably, the aliphatic acid comprises 12-hydroxystearic acid, conjugated linoleic acid, or a mixture thereof.

h. Gums: Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, etc.

The total amount of thickening agents can vary but is typically from about 0.01 to about 20 wt. %, based on the total weight of the composition. In some instances, the total amount of thickening agents is about 0.01 to about 15 wt. %, about 0.01 to about 10 wt. %, about 0.01 to about 0.01 to about 8 wt. %, about 0.01 to about 6 wt. %, about 0.01 to about 5 wt. %, about 0.1 to about 20 wt. %, about 0.1 to about 15 wt. %, about 0.1 to about 10 wt. %, about 0.1 to about 8 wt. %, about 0.1 to about 6 wt. %, or about 0.1 to about 5 wt. %, including ranges and sub-ranges therebetween, based on the total weight of the composition.

In some instances, the compositions include one or more polyacrylate crosspolymers, for example, polyacrylate crosspolymer-6. The total amount of the polyacrylate crosspolymer(s) can vary but may be from about 0.01 to about 10 wt. %, based on the total weight of the compositions. In some instances, the total amount of polyacrylate crosspolymers is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the composition.

In some instances, the compositions include one or more carbomers, which are polymeric materials composed of acrylic acid monomers. The total amount of carbomers may vary but may be from about 0.01 to about 10 wt. %, based on the total weight of the compositions. In some instances, the total amount of carbomers is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the composition.

In some instances, the compositions include acrylamidopropyltrimonium chloride/acrylates copolymer, which is a copolymer of one or more of the monomers formed from the amide of acrylic acid, methacrylic acid and aminopropyltrimethyl-ammonium chloride and one or more monomers of acrylic acid, methacrylic acid or one of their esters. The total amount of acrylamidopropyltrimonium chloride/acrylates copolymer may vary but may be from about 0.01 to about 10 wt. %, based on the total weight of the compositions. In some instances, the total amount of acrylamidopropyltrimonium chloride/acrylates copolymer is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the composition.

In some instances, the compositions include one or more polyquaternium compounds. Non-limiting examples include polyquaternium-10, polyquaternium-11, and polyquaternium-67. The total amount of polyquaternium compounds may vary but may be from about 0.01 to about 10 wt. %, based on the total weight of the compositions. In some instances, the total amount of polyquaternium compounds is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the composition.

In some instances, the compositions include one or more cellulose thickeners (e.g., microcrystalline cellulose, carboxymethylcellulose, hydroxymethylcellulose, and hydroxypropylcellulose). The total amount of cellulose thickeners can vary but may be from about 0.01 to about 10 wt. %, based on the total weight of the compositions. In some instances, the total amount of cellulose thickeners is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the composition.

In some instances, the compositions include polyvinylpyrrolidone (PVP) and/or polyvinylpyrrolidone/vinyl acetate (VP/VA) copolymer. The total amount of PVP and/or VP/VA copolymer can vary but may be from about 0.01 to about 10 wt. %, based on the total weight of the compositions. In some instances, the total amount of PVP and/or VP/VA copolymer is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the composition.

In some instances, the compositions include one or more C8-24 hydroxyl substituted aliphatic acid, C8-24 conjugated aliphatic acid, or a mixture thereof. A non-limiting but preferred example is hydroxystearic acid. Additional examples include conjugated linoleic acid, cis-parinaric acid, trans-7-octadecenoic acid, cis-5,8,11,14,17-eicosapentanoic acid, cis-4,7,10,13,16,19-docosahexenoic acid, columbinic acid, linolenelaidic acid, ricinolaidic acid, stearidonic acid, 2-hydroxystearic acid, alpha-linolenic acid, arachidonic acid, cis-11,14-eicosadienoic acid, linolelaidic acid, monopetroselinic acid, petroselinic acid, ricinoleic acid, trans-vaccenic acid, and a mixture thereof. Further suitable preferred aliphatic acid include cis-11,14,17-eicosatrienoic acid, cis-5-eicosenoic acid, cis-8,11,14-eicosatrienoic acid, hexadecatrienoic acid, palmitoleic acid, petroselaidic acid, trans trans farnesol, cis-13,16-docosadienoic acid, cis-vaccenic acid, cis-11-eicosenoic acid, cis-13,16,19-docosatrienoic acid, cis-13-octadecenoic acid, cis-15-octadecanoic acid, cis-7,10,13,16 docosatetraenoic acid, elaidic acid, gamma-linolenic acid, geranic acid, geranyl geranoic acid, linoleic acid, oleic acid, pinolenic acid, trans-13-octadecenoic acid. More preferably, the aliphatic acid comprises 12-hydroxystearic acid, conjugated linoleic acid, or a mixture thereof. The total amount of C8-24 hydroxyl substituted aliphatic acid(s) and/or C8-24 conjugated aliphatic acid(s) can vary but may be from about 0.1 to about 20 wt. %, about 0.1 to about 15 wt. %, about 0.1 to about 12 wt. %, about 1 to about 20 wt. %, about 1 to about 15 wt. %, about 1 to about 12 wt. %, about 5 to about 20 wt. %, about 5 to about 15 wt. %, or about 5 to about 12 wt. %, including ranges and sub-ranges therebetween, based on the total weight of the composition.

In some instances, the compositions include one or more sucrose fatty esters. A non-limiting but preferred example is sucrose palmitate. Additional examples include sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate. The total amount of sucrose fatty esters can vary but may be from about 0.1 to about 15 wt. %, about 0.1 to about 10 wt. %, about 0.1 to about 8 wt. %, about 1 to about 15 wt. %, about 1 to about 10 wt. %, about 1 to about 8 wt. %, about 2 to about 15 wt. %, about 2 to about 10 wt. %, or about 2 to about 8 wt. %, including ranges and sub-ranges therebetween, based on the total weight of the composition.

In some cases, the compositions are free or essentially free of silicones. For example, the compositions include less than about 3 wt. %, 2 wt. %, 1 wt. %, or 0.5 wt. % of silicones (preferably no silicones). In some cases, the compositions comprise silicones. Non-limiting examples of silicones include amine-functionalized silicones (e.g., amodimethicone), dimethicone, bis-aminopropyl dimethicone, trimethyl silylamodimethicon, etc.

Methods of Treating Hair

The compositions of the instant disclosure are useful for conditioning and/or managing the hair. When the compositions are applied to wet or damp hair they form a lamellar phase in situ. A "lamellar phase" refers generally to packing of polar-headed long chain nonpolar-tail molecules in an environment of bulk polar liquid (i.e., water from the hair), as sheets of bilayers separated by bulk liquid. The compositions can be applied to the wet or damp hair and may be massaged into the hair, for example, with the hands, and/or spread throughout the hair with a comb or brush. This results in a smoothing and softening of the hair, which reduces frizz, dryness, and unwanted volume. The compositions can remain in the hair or can optionally be rinsed from the hair prior to drying and/or styling of the hair.

Another unique aspect of the compositions is that they may be used as a leave-on product. The compositions can be applied to wet or damp hair and allowed to remain on the hair indefinitely, i.e., the hair composition is not removed or rinsed from the hair prior to styling the hair.

The methods of treating hair according to the disclosure also include methods according to various routines. For instance, the compositions may be mixed with a shampoo (or conditioner) prior to application to the hair. Alternatively, the composition may be layered on top of (or lathered into) hair to which the shampoo (or conditioner) is already applied. Furthermore, the composition may be applied separate from the shampoo (or conditioner), i.e., applied to the hair after the shampoo (or conditioner) has been rinsed from the hair. In some instances, it is preferable to treat the hair with a composition of the instant disclosure prior to shampooing the hair, e.g., apply the composition to wet or damp hair prior to application of a shampoo to the hair. The hair may additionally (optionally) be treated with a conditioner after shampooing.

The compositions of the instant disclosure may be incorporated into a kit. For example, the kits may include at least one composition according to the instant disclosure and one or more additional compositions, for example, a shampoo, a conditioner, etc. The various compositions are separately contained in the kits. In some instances, the kits include one or more compositions according the instant disclosure, a shampoo, and/or a conditioner, all of which are separately contained. The kits may also include one or more compositions according the instant disclosure, a shampoo, and a conditioner. Instructions, mixing components, brushes, gloves, measuring tools, etc., may also optionally be included in the kits.

The compositions may be packaged in a variety of different containers, such as, for example, a ready-to-use container. Non-limiting examples of useful packaging include tubes, jars, caps, unit dose packages, and bottles, including squeezable tubes and bottles. The packaging may be configured so that it can be attached to a wall, such as a wall in a bathroom, including walls of a shower or tub. For example, the packaging can be a container that is configured to attach to a wall, such that when pressure is applied to the container, the composition contained therein is expelled from one or more openings in the container. In some cases, the packaging is a tube, such as a tube with two compartments, or dual tubes, each forming a separate compartment. Each compartment may include a different composition. For example, one tube or compartment may include a composition according to the instant disclosure, and the other tube may include a composition to be used with the composition, for example, a shampoo, a conditioner, an all-in-one shampoo/conditioner (i.e., a conditioning shampoo; also referred to as a "co-wash").

In some instances, the compositions of the instant disclosure may be packaged as a spray product, which allows a user to apply the compositions to hair by spraying the composition onto the hair. The compositions are packaged in a spray bottle, which can be a pump spray bottle that is manually actuated or the spray bottle can be pressurized such that the compositions are dispensed from a pressurized aerosol container. A propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

Methods of treating hair according to the disclosure may vary but typically include applying a composition of the instant disclosure to the hair, allowing the composition to remain on the hair for a sufficient amount of time, and rinsing the compositions from the hair. The composition may be applied to the hair in a sequence with other compositions. For example, the compositions may be applied to the hair before shampooing the hair, after shampooing the hair, before conditioning the hair, and/or after conditioning the hair. The compositions, however, are not required to be used in a sequence.

In some cases, the compositions are used in conjunction with additional hair-treatment compositions in a routine, for example, during an individual's normal showering/bathing routine. The composition may be applied to the hair individually or may be combined with one or more additional compositions. Combining the compositions with one or more additional compositions (e.g., a shampoo, a conditioner, a rinse, etc.) can be useful for eliminating multiple steps from a routine. For instance, the composition may be mixed with a shampoo (or conditioner) prior to application to the hair. In this case, the mixture of the shampoo (or conditioner) and the composition are simultaneously applied to the hair during the cleansing or conditioning process and simultaneously rinsed from the hair. Alternatively, the composition may be layered on top of (or lathered into) hair to which a shampoo (or conditioner) has already been applied or vice versa. In this case, the composition may be applied to the hair and without rinsing it from the hair, a shampoo (or conditioner) is then subsequently applied to the hair. Alternatively, the shampoo (or conditioner) may be first applied to the hair and without rinsing the shampoo (or conditioner) from the hair, the hair-treatment composition is also applied to the hair.

When used in conjunction with a shampoo and/or a conditioner, the composition may be mixed or used with the shampoo and/or conditioner in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair-treatment composition of the instant disclosure:shampoo/conditioner, etc.).

The compositions of the instant disclosure may be allowed to remain on the hair for a minimum amount of time before being rinsed from the hair, but it is not necessary to allow the composition to remain on the hair for an extended period of time. Conveniently, the compositions can be applied and allowed to remain on the hair for a period of time that is typical for regular shampooing and/or conditioning. For example, the composition (whether combined with another hair-treatment composition such as a shampoo or conditioner) may be applied to the hair and allowed to remain on the hair for a few seconds (1, 2, 3, or 5 seconds) up to about 1, about 2, about 5, about 10, about 15, about 20, about 25, or about 30 minutes.

When the composition is not being mixed with another composition prior to application to the hair, the composition may be applied to the hair immediately after or before the hair it treated with another composition (e.g., a shampoo and/or a conditioner). For example, the hair-treatment compositions may be applied to the hair within about 1, 2, 5, 10, or 20 minutes before or after a shampoo and/or a conditioner is applied to the hair.

The compositions of the instant disclosure are unique in their ability to provide hair with improved manageability, long-lasting style and frizz control, and smoothness. Accordingly, the instant disclosure relates to methods for treating hair, for example, for improving the manageability of hair, for imparting lasting style and frizz control, and for imparting smoothness. More specifically, the compositions may be used in methods for conditioning the hair, providing curl definition to the hair, providing frizz control to the hair, improving ease of combability and detangling, and providing smoothness.

EMBODIMENTS

In certain embodiments, the compositions of the instant disclosure are transparent and substantially anhydrous cosmetic composition comprising:

about 20 to about 95 wt. %, preferably about 40 to about 90 wt. %, more preferably about 50 to about 90 wt. % of propylene glycol;

about 5 to about 70 wt. %, preferably about 5 to about 50 wt. %, more preferably about 5 to about 40 wt. % of one or more monoalcohols having from 2 to 6 carbon atoms, preferably ethanol;
wherein the weight ratio of the propylene glycol to the monoalcohol(s) (propylene glycol:monoalcohol(s)) is from 20:1 to 1:1, preferably from 20:1 to 1.1:1, more preferably from 18:1 to 2:1;

about 0.1 to about 5 wt. %, preferably about 0.1 to about 4 wt. %, more preferably about 0.1 to 2 wt. % of one or more cationic surfactants;

about 0.1 to about 10 wt. %, preferably about 0.1 to about 5 wt. %, more preferably about 1 to about 0.5 to about 5 wt. % of one or more fatty esters selected from fatty carbonate esters, glycerol fatty esters (glyceryl esters), sucrose fatty esters, sorbitan fatty ester, and fatty acid esters, preferably one or more carbonate esters and/or one or more glycerol fatty esters;

about 0.1 to about 10 wt. %, preferably about 0.1 to about 5 wt. %, more preferably about 0.5 to about 5 wt. % of one or more fatty alcohols selected from cetearyl alcohol, stearyl alcohol, behenyl alcohol, cetyl alcohol, myristyl alcohol, and isostearyl alcohol, preferably myristyl alcohol; and optionally, about 0.1 to about 20 wt. %, preferably about 0.1 to about 15 wt. %, more preferably about 0.1 to about 10 wt. % of one or more thickening agents, for example, one or more thickening agents selected from carboxylic acid or carboxylate based homopolymer or co-polymer, polyquaternium compounds, polyvinylpyrrolidone (PVP) and co-polymers, sucrose esters, polyglyceryl esters, C8-24 hydroxyl substituted aliphatic acid and C8-24 conjugated aliphatic acid, and gums, preferably, polyacrylate crosspolymer, cationic acrylate copolymer, hydroxypropyl cellulose, polyquaterniums, polyvinylpyrrolidone homopolymer/co-polymer, 12-hydroxystearic acid, sugar esters, and polyglycery esters;

wherein the composition is a solubilized, non-emulsified composition until applied to the wet or damp hair, whereupon the composition forms a lamellar phase in situ; and all percentages by weight are based on the total weight of the composition.

The cationic surfactants include those described throughout the instant disclosure but may preferably be selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof. In some instances, the cationic surfactants are preferably selected from cetrimonium chloride, behentrimonium chloride, behentrimonium methosulfate, stearamidopropyl dimethylamine, and a mixture thereof.

In some instances, the cationic surfactants are more preferably selected from cetrimonium chloride, behentrimonium chloride, behentrimonium methosulfate, stearamidopropyl dimethylamine, and a mixture thereof.

Moreover, in some cases, the cationic surfactant is most preferably cetrimonium chloride, behentrimonium chloride, or a mixture thereof.

In addition to propylene glycol, the compositions may optionally include about 0.1 to about 50 wt. %, preferably about 0.1 to about 30, more preferably about 1 to about 20 wt. % of one or more glycols selected from ethylene glycol, butylene glycol, hexylene glycol, pentylene glycol, diethylene glycol, dipropylene glycol, 1,3 propanediol, and glycerin.

In some instances, the compositions include butylene glycol but in other instances, the compositions are free or essentially free of butylene glycol. If present, the total amount of butylene glycol can vary but is typically from about 0.1 to about 50 wt. %, based on the total weight of the composition. In some cases, the total amount of butylene glycol may be about 0.1 to about 40 wt. %, about 0.1 to about 30 wt. %, about 0.1 to about 20 wt. %, about 0.1 to about 10 wt. %, about 1 to about 50 wt. %, about 1 to about 40 wt. %, about 1 to about 30 wt. %, about 1 to about 20 wt. %, or about 1 to about 10 wt. %, including ranges and sub-ranges therebetween, based on the total weight of the composition.

In some cases, the compositions are free or essentially free of silicones. For example, the compositions may include less than about 3 wt. %, 2 wt. %, 1 wt. %, or 0.5 wt. % of silicones (preferably no silicones). Non-limiting examples of silicones include amine-functionalized silicones (e.g., amodimethicone), dimethicone, bis-aminopropyl dimethicone, trimethyl silylamodimethicon, etc.

In certain embodiments, the compositions of the instant disclosure are transparent and substantially anhydrous cosmetic composition comprising:
about 50 to about 95 wt. %, preferably about 55 to about 90 wt. %, more preferably about 60 to about 90 wt. % of propylene glycol;
about 5 to about 70 wt. %, preferably about 5 to about 50 wt. %, more preferably about 5 to about 40 wt. % of ethanol;
wherein the weight ratio of the propylene glycol to the ethanol (propylene glycol:ethanol) is from 20:1 to 1:1, preferably from 20:1 to 1.1:1, more preferably from 18:1 to 2:1;
about 0.1 to about 5 wt. %, preferably about 0.1 to about 4 wt. %, more preferably about 0.1 to 2 wt. % of one or more cationic surfactants, for example one or more cationic surfactants selected from cetrimonium chloride, behentrimonium chloride, behentrimonium methosulfate, stearamidopropyl dimethylamine, and a mixture thereof; even more preferably, cetrimonium chloride, behentrimonium chloride, or a mixture thereof;
about 0.1 to about 10 wt. %, preferably 0.1 to about 5 wt. %, more preferably about 0.5 to about 5 wt. % of one or more fatty esters including:
(i) fatty carbonate esters selected from dialkyl carbonates of formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more dialkyl fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof; and/or (ii) glycerol fatty esters selected from glyceryl caprate, glyceryl caprylate, glyceryl oleate, glyceryl linoleate, glyceryl myristate, glyceryl capromyristate, glyceryl stearate, glyceryl hydroxy stearate, glyceryl isostearate, glyceryl ricinoleate, glyceryl dilaurate, glyceryl dioleate, glyceryldistearate, glycerylmono/dicaprylate, glycerylmono/dimyristate, glycerylstearatepalmitate, glyceryltricaprate/caprylate, caprylic/capricdiglycerylsuccinate, caprylic/capric glycerides, caprylic/capric/isostearic/adipictriglycerides, caprylic/capric/linoleictriglycerides, caprylic/caprictriglycerides, caprylic/capric/stearictriglycerides, glyceryltrilaurate/stearate, glyceryldi/tripalmitostearate, glyceryldi/tritristearate, caprylictriglyceride, caprylic/capric/laurictriglycerides, glyceryltriheptanoate, glyceryl trioctanoate, glyceryl trilaurate, glyceryl trioleate, glyceryltristearate, glyceryltris-12-hydroxystearate, glyceryltriacetyl hydroxystearate, glyceryl triacetyl ricinioleate, glyceryl triisostearate, glyceryl tribehenate, and mixtures thereof;
about 0.1 to about 10 wt. %, preferably about 0.1 to about 5 wt. %, more preferably about 0.5 to about 5 wt. % of one or more fatty alcohols selected from cetearyl alcohol, stearyl alcohol, behenyl alcohol, cetyl alcohol, myristyl alcohol, isostearyl alcohol, and a mixture thereof; and
optionally, about 0.1 to about 20 wt. %, preferably about 0.1 to about 15 wt. %, more preferably about 0.1 to about 10 wt. % of one or more thickening agents, for example, one or more thickening agents selected from carboxylic acid or carboxylate based homopolymer or co-polymer, polyquaternium compounds, polyvinylpyrrolidone (PVP) and co-polymers, sucrose esters, polyglyceryl esters, C8-24 hydroxyl substituted aliphatic acid and C8-24 conjugated aliphatic acid, and gums, preferably, polyacrylate crosspolymer, cationic acrylate copolymer, hydroxypropyl cellulose, polyquaterniums, polyvinylpyrrolidone homopolymer/co-polymer, 12-hydroxystearic acid, sugar esters, and polyglycery esters;
wherein the composition is a solubilized, non-emulsified composition until applied to the wet or damp hair, whereupon the composition forms a lamellar phase in situ; and all percentages by weight are based on the total weight of the composition.

In addition to propylene glycol, the compositions may optionally include about 0.1 to about 50 wt. %, preferably about 0.1 to about 30, more preferably about 1 to about 20 wt. % of one or more glycols selected from ethylene glycol, butylene glycol, hexylene glycol, pentylene glycol, diethylene glycol, dipropylene glycol, 1,3 propanediol, and glycerin In some instances, the compositions include butylene glycol but in other instances, the compositions are free or essentially free of butylene glycol. If present, the total amount of butylene glycol can vary but is typically from about 0.1 to about 50 wt. %, based on the total weight of the composition. In some cases, the total amount of butylene glycol may be about 0.1 to about 40 wt. %, about 0.1 to about 30 wt. %, about 0.1 to about 20 wt. %, about 0.1 to about 10 wt. %, about 1 to about 50 wt. %, about 1 to about 40 wt. %, about 1 to about 30 wt. %, about 1 to about 20 wt. %, or about 1 to about 10 wt. %, based on the total weight of the composition.

In some cases, the compositions are free or essentially free of silicones. For example, the compositions may include less than about 3 wt. %, 2 wt. %, 1 wt. %, or 0.5 wt. % of silicones (preferably no silicones). Non-limiting examples of silicones include amine-functionalized silicones (e.g., amodimethicone), dimethicone, bis-aminopropyl dimethicone, trimethylsilylamodimethicone, etc.

Cationic Surfactants

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonate, stearyl trihydroxyethyl propylenediamine dihydrofluoride, tallowtrimonium chloride, and hexadecyltrimethyl ammonium bromide.

The cationic surfactant(s) may also be chosen from optionally polyoxyalkylenated, primary, secondary or tertiary fatty amines, or salts thereof, and quaternary ammonium salts, and mixtures thereof.

In some cases it is useful to use salts such as chloride salts of the quaternary ammonium compounds.

The fatty amines generally comprise at least one $C_8$-$C_{30}$ hydrocarbon-based chain.

A. Examples of quaternary ammonium salts that may especially be mentioned include: those corresponding to the general formula (III) below:

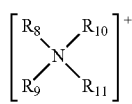
(III)

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

B. a quaternary ammonium salt of imidazoline, such as, for example, those of formula (IV) below:

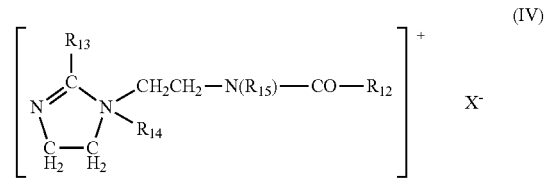
(IV)

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, X is an anion chosen from the group of halides, phosphates, acetates, lactates, alkyl sulfates, alkyl- or alkylarylsulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Rewo;

C. a quaternary diammonium or triammonium salt, in particular of formula (V):

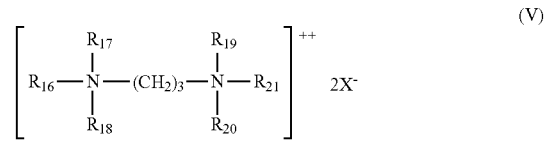
(V)

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group ($R_{16a}$)($R_{17a}$)($R_{18a}$)N—($CH_2$)$_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and X is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), D. Cationic/cationizable surfactants, for example of the general structure

R4-A-R5-B wherein R4 is a saturated or unsaturated, straight or branched alkyl chain with 8 to 24 C atoms, R5 is a straight or branched alkyl chain with 1 to 4 C atoms, A is selected from:

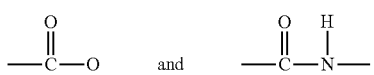

and B is selected from

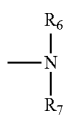

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms,

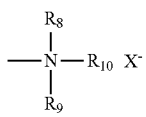

$R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24C atoms, more preferably 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants or amphiphilic surfactants may be chosen from fatty alkylamines, preferably, fatty dialkylamines. In some cases, the fatty dialkylamines may be fatty dimethylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

In some cases the compositions of the instant disclosure include at least one cationic surfactant selected from stearamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereofare useful, especially in combination with fatty dimethylamines such as, for example, stearamidopropyl dimethylamine.

Fatty Compounds

A "fatty compound" is an organic compound that is not soluble in water at normal temperature (25° C.) and at atmospheric pressure (750 mmHg) (solubility below 10%). In some instances, the solubility in water may be below 5%, below 1%, or below 0.1%). Moreover, fatty compounds are generally soluble in one or more organic solvents under the same conditions of temperature and pressure, for example organic solvents such as chloroform, ethanol, benzene or decamethylcyclopentasiloxane.

Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. In some instances, the at least one fatty compound includes one or more fatty alcohols, fatty acids, esters of fatty acids, and/or esters of fatty alcohols (for example, cetyl palmitate, cetyl stearate, myristyl myristate, myristyl stearate, cetyl myristate, and stearyl stearate (a mixture of which is referred to as "cetyl esters")).

Fatty compounds include hydrocarbons, fatty alcohols, fatty alcohol derivatives, fatty acids, fatty acid derivatives, fatty esters, fatty ethers, oils, waxes, etc. The fatty compounds may be liquid or solid at room temperature and at atmospheric pressure (25° C., 1 atm). Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Non-limiting examples of hydrocarbons include linear or branched, optionally cyclic $C_6$-$C_{16}$ alkanes; hexane, undecane, dodecane, tridecane, and isoparaffins, for instance isohexadecane, isododecane and isodecane. Additionally, the linear or branched hydrocarbons may be composed only of carbon and hydrogen atoms of mineral, plant, animal or synthetic origin with more than 16 carbon atoms, such as volatile or non-volatile liquid paraffins, petroleum jelly, liquid petroleum jelly, polydecenes, hydrogenated polyisobutene, and squalane.

The fatty alcohols that can be used may be liquid at 25° C., 1 atm, or may even be solid. They may even be glycerolated and/or oxyalkylenated, and may include from 8 to 30 carbon atoms. They may be saturated or unsaturated. The fatty alcohols useful herein include those having from about 8 to about 30 carbon atoms, from about 12 to about 22 carbon atoms, and from about 14 to about 22 carbon atoms. These fatty alcohols can be straight or branched chain alcohols and can be saturated or unsaturated. Nonlimiting examples of fatty alcohols include decyl alcohol, undecyl alcohol, dodecyl alcohol, myristyl alcohol, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of myristyl alcohol, cetyl alcohol, stearyl alcohol, isostearyl alcohol, oleyl alcohol, isotridecyl alcohol, and a mixture thereof.

The saturated liquid fatty alcohols may be branched. They can optionally comprise, in their structure, at least one aromatic or non-aromatic ring, but are preferably acyclic. Non-limiting examples of liquid saturated fatty alcohols include octyldodecanol, isostearyl alcohol, and 2-hexyldecanol.

The unsaturated liquid fatty alcohols include in their structure at least one double or triple bond and preferably one or more double bonds. When several double bonds are present, there are preferably 2 or 3 of them and they can be conjugated or non-conjugated. These unsaturated fatty alcohols can be linear or branched. They can optionally include in their structure at least one aromatic or non-aromatic ring but they are preferably acyclic. Among liquid unsaturated fatty alcohols, oleyl alcohol, linoleyl alcohol, linolenyl alcohol and undecylenyl alcohol can be cited.

Non-limiting examples of solid fatty alcohols include linear or branched, saturated or unsaturated alcohols containing from 8 to 30 carbon atoms, for example, myristyl alcohol, cetyl alcohol, stearyl alcohol and their mixture, cetylstearyl alcohol.

Non-limiting examples of liquid fatty esters include esters from a $C_6$-$C_{32}$ fatty acid and/or a $C_6$-$C_{32}$ fatty alcohol, and are liquid at 25° C., 1 atm. These esters may be liquid esters of saturated or unsaturated, linear or branched $C_1$-$C_{26}$ aliphatic mono or polyacids and of saturated or unsaturated, linear or branched $C_1$-$C_{25}$ aliphatic mono or polyalcohols, the total number of carbon atoms in the esters being greater than or equal to 10. In some cases, for the esters of monoalcohols, at least one of the alcohol or the acid from which the esters of the invention result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

In some cases, it is particularly useful to include cetyl esters in the hair conditioning compositions. Cetyl Esters is a mixture of the following esters of saturated fatty acids and fatty alcohols: cetyl palmitate, cetyl stearate, myristyl myristate, myristyl stearate, cetyl myristate, and stearyl stearate.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate; diisopropyl sebacate; diisopropyl adipate; di-n-propyl adipate; triisopropyl citrate; glyceryl trilactate; glyceryl trioctanoate; neopentyl glycol diheptanoate; and diethylene glycol diisononanoate.

As oils of plant origin or synthetic triglycerides that may be used in the composition of the invention as liquid fatty esters, the following can be cited, for example, triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, jojoba oil, and shea butter oil.

The solid fatty acid esters and/or fatty acid esters that may be mentioned include solid esters obtained from $C_9$-$C_{26}$ fatty acids and from $C_9$-$C_{25}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

The liquid fatty ethers may be chosen from liquid dialkyl ethers such as dicaprylyl ether. The non-liquid fatty ethers may also be chosen from dialkyl ethers and in particular dicetyl ether and distearyl ether, alone or as a mixture.

Non-limiting examples of waxes include carnauba wax, candelilla wax, esparto wax, paraffin wax, ozokerite, plant waxes such as olive tree wax, rice wax, hydrogenated jojoba wax or absolute flower waxes, such as the blackcurrant blossom essential wax sold by Bertin (France), or animal waxes such as beeswaxes or modified beeswaxes (cerabellina), and ceramides. Non-limiting examples of ceramides include N-linoleyldihydrosphingosine, N-oleyldihydrosphingosine, N-palmityldihydrosphingosine, N-stearyldihydrosphingosine or N-behenyldihydrosphingosine, or mixtures of these compounds.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof.

In some cases, the one or more fatty compounds may be one or more high melting point fatty compounds. A high melting point fatty compound is a fatty compound having a melting point of greater than 25° C. Even higher melting point fatty compounds may also be used, for example, fatty compounds having a melting point of 30° C. or higher, 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Non-limiting examples of the high melting point compounds are found in International Cosmetic Ingredient Dictionary, Fifteenth Edition, 2014, which is incorporated herein by reference in its entirety. The fatty alcohols useful herein are those having from about 12 to about 30 carbon atoms, preferably from about 14 to about 22 carbon atoms. These fatty alcohols are saturated and can be straight or branched chain alcohols. Non-limiting examples of high melting point fatty compounds include fatty alcohols such as, for example, myristyl alcohol (having a melting point of about 38° C.), cetyl alcohol (having a melting point of about 56° C.), stearyl alcohol (having a melting point of about 58-59° C.), behenyl alcohol (having a melting point of about 71° C.), and mixtures thereof. These compounds are known to have the above melting points. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are myristyl alcohol, cetyl alcohol, stearyl alcohol and mixtures thereof.

In an embodiment, the fatty alcohol in the compositions of the present disclosure comprises myristyl alcohol.

Implementation of the present disclosure is provided by way of the following examples. The examples serve to illustrate the technology without being limiting in nature.

|  | INCI US | A wt. % | B wt. % | C wt. % | D wt. % | E wt. % |
|---|---|---|---|---|---|---|
| Mono-alcohol | ETHANOL AND/OR ISOPROPYL ALCOHOL | 28.1 | 28.7 | 20 | 20 | 20.1 |
| PG | PROPYLENE GLYCOL | 65 | 65 | 75.3 | 73.7 | 73 |
|  | Ratio of PG/Monoalcohols | 2.3 | 2.3 | 3.8 | 3.7 | 3.7 |
| Cationic Surfactant | CETRIMONIUM CHLORIDE, BEHENTRIMONIUM CHLORIDE, AND/OR STEARAMIDOPROPYL DIMETHYLAMINE | 1.2 | 0.6 | 0.6 | 0.6 | 1.2 |
| Fatty Esters | DICAPRYLYL CARBONATE AND/OR CAPRYLIC/CAPRIC TRIGLYCERIDE | 0.9 | 0.9 | 0.9 | 0.9 | 0.9 |
| Fatty Alcohol | MYRISTYL ALCOHOL | 2 | 2 | 2 | 2 | 2 |
| Misc. | PRESERVATIVES, FRAGRANCE, SALTS, pH ADJUSTERS, NONIONIC SURFACTANTS, ETC. | ≤2 | ≤2 | ≤2 | ≤2 | ≤2 |
| Water | WATER | 1.8 | 1.8 | 0 | 1.8 | 1.8 |

|  | INCI US | F | G | H |
|---|---|---|---|---|
| Mono-alcohols | ETHANOL AND/OR ISOPROPYL ALCOHOL | 5 | 20 | 10 |
| PG | PROPYLENE GLYCOL | 20 | 40 | 65 |
|  | Ratio of PG/Monoalcohols | 4 | 2 | 6.5 |
| Glycols | BUTYLENE GLYCOL AND/OR HEXYLENE GLYCOL AND/OR PENTYLENE GLYCOL AND/OR 1,3 PROPANEDIOL AND/OR CAPRYLYL GLYCOL AND/OR GLYCERIN | 50-60 | 50-60 | 50-60 |
| Cationic Surfactants | CETRIMONIUM CHLORIDE AND/OR BEHENTRIMONIUM CHLORIDE AND/OR BHENTRIMONIUM METHOSULFATE AND/OR STEARAMIDOPROPYL DIMETHYLAMINE | 0.5-3 | 0.5-3 | 0.5-3 |
| Fatty Esters | DICAPRYLYL CARBONATE AND/OR CAPRYLIC/CAPRIC TRIGLYCERIDE | 0.5-1 | 0.5-1 | 0.5-1 |
| Fatty Alcohol | MYRISTYL ALCOHOL AND/OR CETYL ALCOHOL | 1-4 | 1-4 | 1-4 |
| Misc. | PRESERVATIVES, FRAGRANCE, SALTS, pH ADJUSTERS, NONIONIC SURFACTANTS, ETC. | ≤2 | ≤2 | ≤2 |
| Water | WATER | ≤4 | ≤4 | ≤4 |

|  | INCI US | I | J | K | L | M | N | O |
|---|---|---|---|---|---|---|---|---|
| EtOH | ETHANOL | 28.7 | 28.7 | 20 | 20 | 20 | 5 | 10 |
| PG | PROPYLENE GLYCOL | 64 | 64 | 68.7 | 73.4 | 73.5 | 86.7 | 83.5 |
|  | Ratio of PG/Monoalcohols | 2.2 | 2.2 | 3.4 | 3.7 | 3.7 | 17.3 | 8.4 |
| Cationic Surfactant | CETRIMONIUM CHLORIDE | 0.6 | 0.6 | 0.6 | 0.6 | 0.6 | 0.6 | 0.6 |
| Fatty Esters | DICAPRYLYL CARBONATE | 0.9 | 0.9 | 0.9 | 0.9 | 0.9 | 0.9 | 0.9 |
| Fatty Alcohol | MYRISTYL ALCOHOL | 2 | 2 | 2 | 2 | 2 | 2 | 2 |
| Thickening Agents | POLYACRYLATE CROSSPOLYMER-6, CARBOMER, CATIONIC ACRYLATES COPOLYMER*, HYDROXYPROPYL-CELLULOSE, POLYQUATERNIUM-11, AND/OR POLYQUATERNIUM-10 | 0.1-2 | 0.1-2 | 0.1-2 | 0.1-2 | 0.1-2 | 0.1-2 | 0.1-2 |

|  |  |  |  |  |  |  |  |
|---|---|---|---|---|---|---|---|
| Solvent | ISOHEXADECANE | | | 1.3 | | | |
| Misc. | PRESERVATIVES, FRAGRANCE, SALTS, pH ADJUSTERS, NONIONIC SURFACTANTS, ETC. | ≤2 | ≤2 | ≤2 | ≤2 | ≤2 | ≤2 |
| Water | WATER | 1.8 | 1.8 | 3 | 1.8 | 1.8 | 3.4 | 1.8 |

| | INCI US | P | Q | R | S | T | U |
|---|---|---|---|---|---|---|---|
| EtOH | ETHANOL | 10 | 5 | 5 | 5 | 20 | 10 |
| PG | PROPYLENE GLYCOL | 83.5 | 87.7 | 86.7 | 87.7 | 72.7 | 82.6 |
| | Ratio of PG/Monoalcohols | 8.4 | 17.5 | 17.3 | 17.5 | 3.6 | 8.3 |
| Cationic Surfactants | CETRIMONIUM CHLORIDE AND/OR BEHENTRIMONIUM CHLORIDE | 0.6 | 0.6 | 0.6 | 0.6 | 1.2 | 1.2 |
| Fatty Esters | DICAPRYLYL CARBONATE | 0.9 | 0.9 | 0.9 | 0.9 | 0.9 | 0.9 |
| Fatty Alcohol | MYRISTYL ALCOHOL | 2 | 2 | 2 | 2 | 2 | 2 |
| Thickening Agents | POLYQUATERNIUM-67, PVP, VP/VA COPOLYMER, AND/OR HYDROXYPROPYL-CELLULOSE | 0.1-2 | 0.1-2 | 0.1-2 | 0.1-2 | 0.1-2 | 0.1-2 |
| Misc. | PRESERVATIVES, FRAGRANCE, SALTS, pH ADJUSTERS, NONIONIC SURFACTANTS, ETC. | ≤2 | ≤2 | ≤2 | ≤2 | ≤2 | ≤2 |
| Water | WATER | 1.8 | 1.8 | 2.8 | 1.8 | 1.8 | 1.8 |

| | INCI US | V | W | X |
|---|---|---|---|---|
| Alcohols | ETHANOL AND/OR ISOPROPYL ALCOHOL | 30 | 50 | 20 |
| PG | PROPYLENE GLYCOL | 15 | 15 | 15 |
| Glycols | BUTYLENE GLYCOL AND/OR CAPRYLYL GLYCOL AND/OR GLYCERIN | 50-60 | | 50-60 |
| | Ratio of PG/Monoalcohols | 0.5 | 0.3 | 0.8 |
| Cationic Surfactants | CETRIMONIUM CHLORIDE, BEHENTRIMONIUM CHLORIDE, AND/OR BEHENTRIMONIUM METHOSULFATE | 0.5-1.5 | 2-3 | 0.5-1.5 |
| Fatty Esters | DICAPRYLYL CARBONATE, CAPRYLIC/CAPRIC TRIGLYCERIDE, AND/OR ISOPROPYL MYRISTATE | 0.9 | 7.4 | 0.9 |
| Fatty Alcohol | MYRISTYL ALCOHOL, CETYL ALCOHOL, AND/OR CETEARYL ALCOHOL | 2 | 12 | 2 |
| Silicone & Nonionic Surfactant | PEG-14 DIMETHICONE & PPG-10 METHYL GLUCOSE ETHER | | 2 | |
| Misc. | PRESERVATIVES, FRAGRANCE, SALTS, pH ADJUSTERS, NONIONIC SURFACTANTS, ETC. | ≤2 | ≤2 | ≤2 |
| | WATER | ≤4 | ≤10 | ≤4 |

*ACRYLAMIDOPROPYLTRIMONIUM CHLORIDE/ACRYLATES COPOLYMER

Hair swatches were treated with Composition B, D, or X and the deposition of key ingredients on the hair was determined. After hair swatches were shampooed with a standard shampoo, Compositions B, D, or X was applied to the damp hair swatches. The composition was applied to the hair swatches and massaged into the hair swatch for about 10 seconds, after which the hair swatches were rinsed with water and dried.

The amount of cationic surfactant was determined using LC-MS/MS analysis. Approximately half of each swatch was homogenized by cutting the hair from root to tip into 2 mm sections. Approximately 20 mg of homogenized hair sample was weighed into Eppendorf tubes and extracted using IPA and a Thermomixer set to 30° C. for 3 hours. The samples were analyzed via LC-MS/MS in duplicate.

The amount of fatty esters, fatty alcohols, and glycols were determined using GC-MS analysis. Approximately 20 mg of homogenized hair sample was weighed into Eppendorf tubes and extracted using acetone and Thermomixer set to 50° C. for 5 hours. The samples were analyzed via GC-MS in duplicate or triplicate. The total amount of key ingredient per formula (wt. %), is shown in the table below.

|  | B | D | X |
|---|---|---|---|
| Cationic Surfactant | 0.6 | 0.6 | 0.6 |
| Fatty Esters and Fatty alcohol | 2.9 | 2.9 | 2.7 |
| Glycols (propylene glycol and/or butylene glycol) | 65 | 73.7 | 66.6 |
| Solvent (H₂O/Alcohol) | 30.5 | 21.8 | 24 |

The results of the deposition analysis are presented in the table below. The values represent g/g of hair (ppm).

|  | B | D | X |
|---|---|---|---|
| Cationic Surfactant | 1402.6 | 1404.1 | 949.0 |
| Fatty Alcohol | 1277.1 | 1147.5 | 902.9 |
| Fatty Esters | 150 | 128.8 | 67.8 |

Finally, the table below presents the data as the percent (%) of active compound deposited relative to the amount in the original formulation.

|  | Cationic Surfactant | Fatty Alcohol | Fatty Esters | Total Active |
|---|---|---|---|---|
| Composition B | 23.4 | 6.4 | 1.7 | 31.4 |
| Composition D | 23.4 | 5.7 | 1.4 | 30.6 |
| Comparative Composition X | 17.1 | 4.9 | 0.8 | 22.8 |

The data shows that treatment with Composition B resulted in the highest deposition off all of the cationic surfactant, the fatty alcohol, and the fatty ester, followed by Composition D. Treatment with Comparative Composition X resulted in the least amount of deposited active ingredients. Depositing higher amounts of cationic surfactant, the fatty alcohol, and the fatty ester, onto the hair results in better sensorial properties such as shine, nourishment, ease of styling, and ease of detangling.

Example 6

(Comparative Testing with Commercial Benchmark Product A

Comparative testing was carried out to compare treatment with Composition B with a commercial benchmark product (Commercial Benchmark A), which is a rinse-off conditioning product having the ingredients shown below.

Ingredients for Commercial Benchmark a (Listed in the Order as Presented on the Packaging):

Butylene Glycol, Alcohol, Propylene Glycol, Water, Glycerin, Hydrolyzed Collagen, Myristyl Alcohol, Steartrimonium Chloride, Parfum, Cetrimonium Chloride, Dicaprylyl Carbonate, Hydroxyethyl Urea. The commercial product additionally contains other ingredients such as Hydrolyzed Protein, Plant extracts, Amino Acids, and Gum.

A total of six (6) volunteers with medium-long to very-long hair participated in the study. Volunteers were instructed to remove excess water from their hair after shampooing. On half of the head, the participants applied Composition B to the damp hair and on the other half of the head volunteers applied the commercial benchmark product. Each composition was massaged into the hair by hand for about 9 seconds. The hair was then rinsed and blow dried.

The volunteers then evaluated the hair with respect to a variety of cosmetic attributes. Composition B performed in parity (no statistical difference) with the commercial benchmark product for most attributes. Composition B, however, showed a statistically significant improvement with respect to absorption, supple in product, mass effect, and body (feel). The commercial benchmark product, however, showed a statistically significant improvement with respect to distribution to ends, quick hair changes, and surface effect. The commercial benchmark product was also found to be more sticky than Composition B.

Example 7

Comparative Testing with Commercial Benchmark Product B

Comparative testing was carried out to compare treatment with Composition B with a commercial benchmark product B (Commercial Benchmark B), which is a rinse-off conditioning product having the ingredients shown below.

Ingredients for Commercial Benchmark Product B (Listed in the Order as Presented on the Packaging):

Butylene Glycol, Ethanol, Glycerin, Propylene Glycol, Purified Water, Steartrimonium Chloride, Myristyl Alcohol, Dicaprylyl Carbonate. The commercial product additionally contains other ingredients such as Plant Extracts, Hydrolyzed Proteins, Sodium PCA, Betaine, Sorbitol, Amino Acids, Plant Oils, Ceramide, Fragrance.

A total of six (6) volunteers with medium-long to very-long hair participated in the study. Volunteers were instructed to remove excess water from their hair after shampooing. On half of the head, the participants applied Composition B to the damp hair and on the other half of the head volunteers applied the commercial benchmark product. Each composition was massaged into the hair by hand for about 9 seconds. The hair was then rinsed and blow dried.

The volunteers then evaluated the hair with respect to a variety of cosmetic attributes. Composition B performed largely in parity (no statistical difference) with the commercial benchmark product for most attributes. The commercial benchmark product, however, showed a statistically significant improvement with respect to ease of blow drying, ease of shaping, better shape, and better visual smoothness.

Example 8

Comparative Testing with Commercial Benchmark Product C

Comparative testing was carried out to compare treatment with Composition A with a commercial benchmark product C (Commercial Benchmark C, which is an aqueous, rinse-off conditioning product containing at least 50% by weight of water based on the total weight of the product. Commercial Benchmark Product C is prepared by mixing the two formulations (Part A and Part B) shown below and is sprayed on cleaned and dried hair (towel dried or thoroughly dried) and rinsed right away. Part A and Part B are mixed in a ratio of about 2:1. For this study, 6 grams of Part A was mixed with 3 grams of Part B.

|  | INCI US | wt. % |
|---|---|---|
| PART A |  |  |
| Glycol | GLYCERIN AND BUTYLENE GLYCOL | 1.1 |
| Cationic Surfactant | CETRIMONIUM CHLORIDE | 1.5 |
| Nonionic Surfactants | TRIDECETH-10 AND TRIDECETH-5 | 2 |

-continued

| | INCI US | wt. % |
|---|---|---|
| Silicon | AMODIMETHICONE | 4.4 |
| Misc. | PRESERVATIVES, FRAGRANCE, SALTS, pH ADJUSTERS, COLORANTS, ETC. | ≤2 |
| Water | WATER | 90.5 |
| PART B (Booster) | | |
| Mono-alcohol | ETHANOL AND ISOPROPYL ALCOHOL | 14 |
| Glycol | GLYCERIN | 5.2 |
| Cationic Surfactant | BEHENTRIMONIUM CHLORIDE | 1.6 |
| Nonionic Surfactants | C11-15 PARETH-7, LAURETH-9, PEG-8, TRIDECETH-12, AND/OR PEG-8 ISOSTEARATE | 2.8 |
| Silicones | AMODIMETHICONE AND CYCLOPENTASILOXANE | 4.7 |
| Oils | *SIMMONDSIA CHINENSIS* (JOJOBA) SEED OIL, *HELIANTHUS ANNUUS* (SUNFLOWER) SEED OIL, AND/OR *PERSEA GRATISSIMA* (AVOCADO) OIL | 10.5 |
| Misc. | PRESERVATIVES, FRAGRANCE, SALTS, pH ADJUSTERS, EXTRACTS, ETC. | ≤2 |
| Water | WATER | 61 |

A total of six (6) volunteers with medium-long to very-long hair participated in the study. Volunteers were instructed to remove excess water from their hair after shampooing. On half of the head, the participants applied Composition B to the damp hair and on the other half of the head volunteers applied the commercial benchmark product. Each composition was massaged into the hair by hand for about 9 seconds. The hair was then rinsed and blow dried.

The volunteers then evaluated the hair with respect to a variety of cosmetic attributes. Composition A performed largely in parity (no statistical difference) with the commercial benchmark product for most attributes. Statistical differences between the products was that hair treated with Composition A was rated as more smooth and soft during rinsing, the hair appeared to be more coated and the coating was more even (uniform), and the hair fibers exhibited better alignment. Hair treated with the commercial benchmark product was less dehydrated and slightly softer.

Example 9

Consumer Testing

Consumer testing was carried out in Germany to determine how consumers evaluated the following composition.

| | INCI US | Y wt. % |
|---|---|---|
| Mono-alcohol | ETHANOL | 20 |
| PG | PROPYLENE GLYCOL | 73 |
| | Ratio of PG/Monoalcohols | 3.7 |
| Cationic Surfactant | CETRIMONIUM CHLORIDE AND BEHENTRIMONIUM CHLORIDE | 1.2 |
| Fatty Esters | DICAPRYLYL CARBONATE | 0.9 |
| Fatty Alcohol | MYRISTYL ALCOHOL | 2 |
| Misc. | PRESERVATIVES, FRAGRANCE, SALTS, pH ADJUSTERS, | ≤2 |

-continued

| | INCI US | Y wt. % |
|---|---|---|
| | NONIONIC SURFACTANTS, ETC. | |
| | WATER | 1.8 |

40 women from age 20 to age 54 participated in the study. The length and type of hair varied widely and included short, long, straight, wavy, curly, natural, bleached, and colored hair. Participants followed a two week procedure. During the first week, participants were instructed to shampoo their hair according to their regular schedule. Instead of using their regular conditioner, participants were instructed to use Composition Y. After shampooing the hair, while the hair was wet/damp, participants applied Composition Y in an amount sufficient to saturate the hair. After thoroughly massaging Composition Y into the hair (no need for a leave in time) the hair was rinsed with water and styled according to the participants usual routine. The protocol for the second week was the same as the first week except that participants were instructed to condition their hair with their regular conditioner after treatment with Composition Y, i.e., after rinsing Composition Y from the hair, the participants conditioned their hair.

The participants evaluated their for a variety of attributes, which are summarized in the table below.

| Attribute | 1st week: Product used alone | 2nd week: Product used with a conditioner |
|---|---|---|
| Detangles upon rinsing | Immediate results are seen right after application and after rinsing | No difference with $1^{st}$ week |
| Softness | Hair is very soft Intense softness | Some women report that their hair is too soft |
| Lightness & Volume | For the majority, hair feels lighter than with current product and with more volume for all types of hair | Some women report that their hair is heavier and loses elasticity; some women reported that their hair is overloaded with products |
| Leaves my hair shiny | Very shiny hair after each use throughout the test | No difference with $1^{st}$ week |
| Strength | More supple, thicker hair | No difference with $1^{st}$ week |
| Easy to comb | Hair is easy to comb | Tendency to be even easier than in $1^{st}$ week |
| Cleanliness | Yes, not making hair greasy | Feeling of overload/heavier hair could lead to less cleanliness feeling |

The data show an improvement in all attributes during the first week of use. Many of the improvements carried into the second week, when participants added-back their regular conditioner. The data show that adding-back a conditioner, however, did not necessarily further improve the attributes, but in some instances, caused the hair to feel too heavy and overloaded.

Example 10

Consumer Testing

Consumer testing was carried out in the United States to determine how consumers evaluated Composition Y, which is described above in Example 8. 96 women participated in the study. The length and type of hair varied widely and included short, long, straight, wavy, curly, natural, bleached, and colored hair. The two-week protocol as used in Example 8 was used in the instant study. The participants evaluated their hair for a variety of attributes, which are summarized in the table below.

| N = 96 | Shine | Soft | Healthy | Moisturized | Voluminous | Strong | Frizz-Free | Lightweight |
|---|---|---|---|---|---|---|---|---|
| Current Routine | 29 | 42 | 37 | 26 | 24 | 31 | 19 | 37 |
| Week 1 | 74 | 80 | 67 | 62 | 51 | 62 | 58 | 71 |
| Week 2 | 80 | 83 | 80 | 83 | 60 | 73 | 71 | 67 |

The values in each column represent the number of individuals that reported the attribute. For example, with respect to shine, 29 individuals reported shine while using their current routine. However, during week 1 of treatment, the number of individuals reporting shine jumped to 74; and during week 2 of treatment, the number of individuals reporting shine jumped to 80.

The data show a marked improvement using Composition Y compared the participants regular routine for all attributes. In nearly all instances, the improvements were even more significant during the second week of the study.

Example 11

Thickened Versus Non-Thickened Compositions

A study was carried out to determine the differences between hair treatments with Composition E and hair treatments with thickened Composition P. Composition P has a thicker consistency than Composition E, due to the inclusion of polyquaternium-67. A total of 10 volunteers with medium-long to very-long hair participated in the study. Volunteers were instructed to remove excess water from their hair after shampooing. On half of the head, the participants applied Composition E to the damp hair and on the other half of the head the participants applied Composition P to the damp hair. Each composition was massaged into the hair by hand for 9 seconds. The hair was then rinsed and blow dried. The participants then evaluated the hair with respect to a number of cosmetic attributes.

Both Composition E and Composition P provided similar results in most respects. For example, both compositions provided the hair with improved smoothness and discipline. Composition P provided a statistically significant improvement with respect to consistency and improvements to dry coated hair. Composition E, on the other hand, provided statistically significant improvements with respect to suppleness of the product and ease of passing fingers through the hair.

Example 12

Humidity Study

Compositions 1-7, which appear in the table below, were prepared.

|  | INCI US | 1 | 2 | 3 | 4 | 5 | 6 | 7 |
|---|---|---|---|---|---|---|---|---|
| EtOH | ETHANOL | 20 | 20 | 10 | 10 | 10 | 10 | 20 |
| PG | PROPYLENE GLYCOL | 73.7 | 73.5 | 83.5 | 82.7 | 82.5 | 82.3 | 72.7 |
|  | Ratio of PG/Monoalcohols | 3.7 | 3.7 | 8.4 | 8.3 | 8.3 | 8.2 | 3.6 |
| Cationic Surfactant | CETRIMONIUM CHLORIDE | 0.6 | 0.6 | 0.6 | 0.6 | 0.6 | 0.6 | 0.6 |
| Fatty Ester | DICAPRYLYL CARBONATE | 0.9 | 0.9 | 0.9 | 0.9 | 0.9 | 0.9 | 0.6 |
| Fatty Alcohol | MYRISTYL ALCOHOL | 2 | 2 | 2 | 2 | 2 | 2 | 2 |
| Thickening Agents | POLYQUATERNIUM-67 |  |  | 0.2 |  |  |  |  |
|  | PVP/VA COPOLYMER |  |  |  | 1 | 1 | 1 | 1 |
|  | HYDROXYPROPYL-CELLULOSE |  | 0.2 |  |  | 0.2 | 0.4 |  |
| Misc. | PRESERVATIVES, FRAGRANCE, SALTS, pH ADJUSTERS, ETC. | ≤2 | ≤2 | ≤2 | ≤2 | ≤2 | ≤2 | ≤2 |
| Water | WATER | 1.8 | 1.8 | 1.8 | 1.8 | 1.8 | 1.8 | 1.8 |

Bleached hair swatches were shampooed with a standard shampoo, rinsed, and treated with Compositions 1-7. Approximately 1 gram of Compositions 1, 2, 3, 4, 5, 6, or 7 was applied to the wet hair swatches (2.7 grams). The compositions was applied to the wet hair swatches and massaged into the hair swatch to ensure coverage. The hair swatches were allowed to air dry overnight at room temperature then subsequently placed in a humidity chamber for 20 hours (25° C., 80% humidity). After being subjected to treatment with humidity for 20 hours, the hair swatches were visually evaluated for frizziness/volume. Pictures of the hair swatches before and after treatment with humidity are provided in FIG. 1. The hair swatches treated with Compositions 4, 5, 6, and 7 exhibited significantly less frizz/less volume than hair swatches treated with Compositions 1, 2 and 3. The data illustrates that inclusion of PVP/VA copolymer significantly improves the anti-frizz/anti-volume properties (improves hair manageability) on its own, and especially when combined with hydroxylpropyl cellulose.

Example 13

Smoothing Study

Compositions 1-10, which appear in the table below, were prepared.

|  | INCI US | 1 | 2 | 3 | 4 | 5 | 6 | 7 | 8 | 9 | 10 |
|---|---|---|---|---|---|---|---|---|---|---|---|
| EtOH | ETHANOL | 20 | 20 | 20 | 15 | 15 | 15 | 15 | 15 | 15 | 20 |
| PG | PROPYLENE GLYCOL | 73.7 | 73.5 | 73.4 | 78.4 | 78.4 | 78.5 | 76.2 | 75.7 | 73.7 | 68.7 |
|  | Ratio of PG/Monoalcohols | 3.7 | 3.7 | 3.7 | 5.2 | 5.2 | 5.2 | 5.1 | 5 | 4.9 | 3.4 |
| Cationic Surfactant | CETRIMONIUM CHLORIDE | 0.6 | 0.6 | 0.6 | 0.6 | 0.6 | 0.6 | 0.6 | 0.6 | 0.6 | 0.6 |
| Fatty Esters | DICAPRYLYL CARBONATE | 0.9 | 0.9 | 0.9 | 0.9 | 0.9 | 0.9 | 0.9 | 0.9 | 0.9 | 0.9 |
| Fatty Alcohol | MYRISTYL ALCOHOL | 2 | 2 | 2 | 2 | 2 | 2 | 2 | 2 | 2 | 2 |
| Thickening Agents | ACRYLAMIDOPROPYL-TRIMONIUM CHLORIDE/ACRYLATES COPOLYMER |  |  |  | 0.04 | 0.04 |  | 1.1 | 1.3 | 2.2 | 2.2 |
|  | HYDROXYPROPYL-CELLULOSE |  | 0.2 | 0.4 | 0.2 | 0.2 | 0.2 |  |  |  |  |
|  | SILICA |  |  |  | ≤0.01 |  |  |  |  |  |  |
|  | ISOHEXADECANE |  |  | ≤0.01 | ≤0.01 |  |  | 0.7 | 0.8 | 1.3 | 1.3 |
| Misc. | PRESERVATIVES, FRAGRANCE, SALTS, pH ADJUSTERS, NONIONIC SURFACTANTS, ETC. | ≤2 | ≤2 | ≤2 | ≤2 | ≤2 | ≤2 | ≤2 | ≤2 | ≤2 | ≤2 |
| Water | WATER | 1.8 | 1.8 | 1.8 | 1.8 | 1.8 | 1.8 | 2.4 | 2.6 | 3.1 | 3.1 |
|  | VISCOSITY M2 (DU) | NM[1] | 25 | 23.6 | 24.3 | 19.2 | 28.8 | 20.5 | 30.1 | 129 | 95.5 |

[1]Not Measureable

Figure 2:
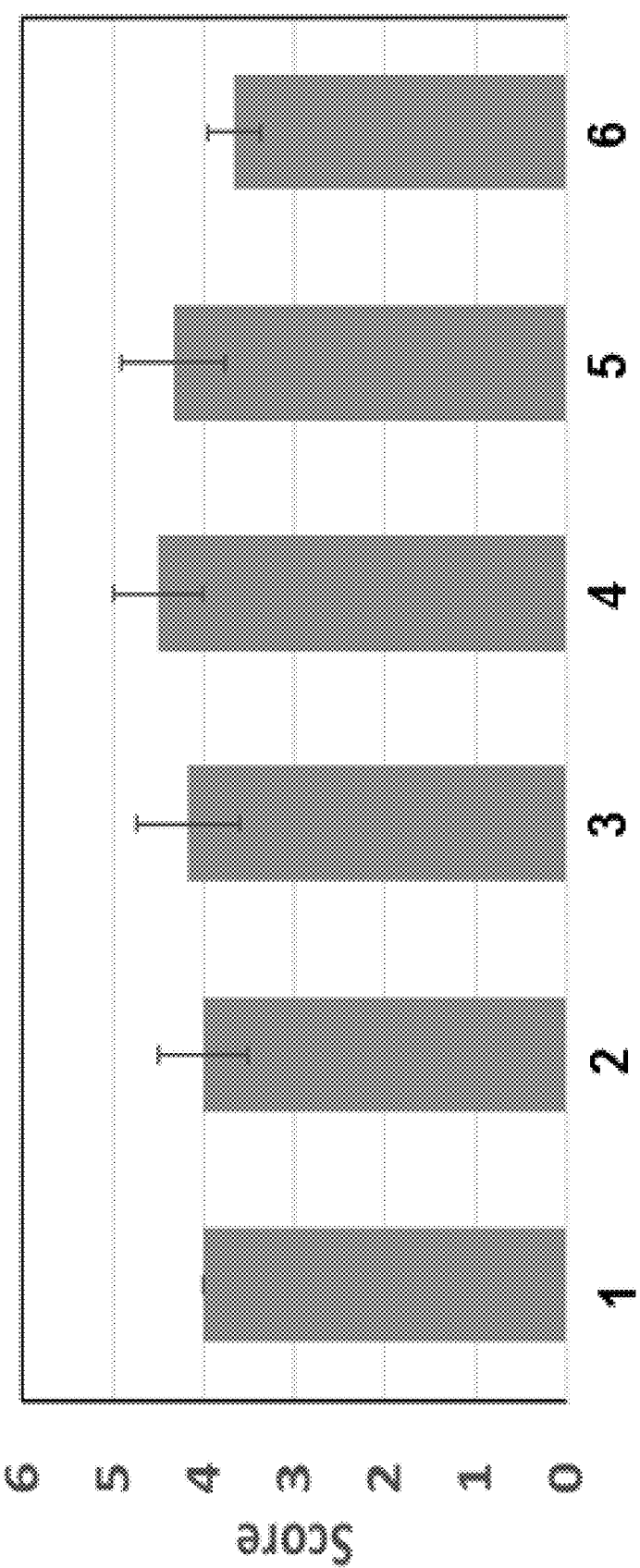
FIG. 2 compares the smoothness of hair swatches treated with compositions according to the instant disclosure.

Composition 1-6 were selected for further testing. Bleached hair swatches were shampooed with a standard shampoo, rinsed, and treated with Compositions 1-6. Approximately 1 gram of Compositions 1, 2, 3, 4, 5, or 6, was applied to the wet hair swatches. The compositions was applied to the wet hair swatches and massaged into the hair swatch to ensure coverage. The hair swatches were allowed to air dry and then evaluated for smoothness on a scale of 1-5, where 1 represents the smoothness of hair swatches that were shampooed but not further treated, and 5 represents complete smoothness (the higher the number the better the smoothness). Smoothness was evaluated by a trained panel of experts. Experts ranked the smoothness of the hair on a scale of 1 to 5, where 5 represents perfect smoothness and 1 represents smoothness after shampooing (no conditioning). The results are graphically shown in FIG. 2.

Example 14

Curl Detangler Study

A curl detangler study was carried out to determine how Inventive Composition U of Example 3 performed in a side-by-side comparison with a popular commercial benchmark product used for detangling curly hair. The commercial benchmark product is an aqueous composition that contains silicone and does not form a lamellar phase in situ. Twelve African-American women volunteers with hair characterized as having a coily curl pattern participated in the study. All volunteers were at least eighteen years old and reported regularly using hair detangler products. The volunteers were instructed to use Inventive Composition U or the commercial benchmark product for ten days. Subsequently, the volunteers used the other product for ten days according to their regular routine. The products were applied to wet or damp hair and massaged and/or combed throughout the hair to smooth and detangle the hair. After smoothing and detangling, the hair was cleansed, optionally conditioned, and styled according to the volunteers' regular routine. The volunteers did not know that one product represented an inventive composition according to the instant disclosure and one product represented a commercial benchmark product. Furthermore, volunteers were randomly assigned which product to use for the first ten days and which product to use for the second ten days. The volunteers ranked the products. The results are presented in the table below.

|  | Commercial Benchmark Product | Inventive Composition U |
|---|---|---|
| Overall Liking | — | ○ |
| Compared to Other Detangler Products | — | ○ |
| Product Preference | X | ○ |

"○" represents the best performer
"—" represents acceptable performance but not the best
"X" represents the worste performer In addition to the results above, volunteers ranked Inventive Composition U higher on a five star scale in terms of overall satisfaction, appeal, and effectiveness (3.5 for the commercial benchmark products versus 4.1 for Inventive Composition U). Volunteers also reported that Inventive Composition U performed better than the commercial benchmark product in terms of not shrinking hair, moisturizing effect, strengthening hair, and reducing routine time. Inventive Composition U was also observed by the volunteers as being lightweight, effective at detangling and making their hair soft, smooth and moisturized The terms "comprising," "having," and "including" are used in their open, non-limiting sense.

The terms "a" and "the" are understood to encompass the plural as well as the singular.

The compositions and methods of the present disclosure can comprise, consist of, or consist essentially of the essential elements and limitations of the disclosure described herein, as well as any additional or optional ingredients, components, or limitations described herein or otherwise useful.

The compositions described throughout this disclosure may be a "leave-on" product. A "leave-on" (also called leave-in) product refers to a hair treatment composition that is applied to hair and is not subjected to immediate rinsing and/or washing for at least 4 hours or for a period of time ranging from 4 hours up to 72 hours, from 4 hours up to 48 hours, or from 8 hours up to 36 hours, or from 8 hours up to 24 hours. In other words, the product is applied to the hair and remains on the hair, as styled, i.e., it is not removed from the hair prior to styling the hair.

All percentages, parts and ratios herein are based upon the total weight of the compositions of the present disclosure, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "substantially free" or "essentially free" as used herein means that there is less than about 5% by weight of a specific material added to a composition, based on the total weight of the compositions. Nonetheless, the compositions may include less than about 2 wt. %, less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

"Cosmetically acceptable" means that the item in question is compatible with a keratinous substrate such as skin and hair. For example, a "cosmetically acceptable carrier" means a carrier that is compatible with a keratinous substrate such as skin and hair.

Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counter-ion. This list of counter-ions, however, is non-limiting.

The expression "inclusive" for a range of concentrations means that the limits of the range are included in the defined interval.

"Volatile", as used herein, means having a flash point of less than about 100° C.

"Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the compositions (nanoemulsions) of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A transparent and substantially anhydrous cosmetic composition comprising:
   50 to 90 wt. % of propylene glycol;
   5 to 30 wt. % of one or more monoalcohols having from 2 to 6 carbon atoms;
      wherein the weight ratio of the propylene glycol to the monoalcohol(s) (propylene glycol:monoalcohol(s)) is from 20:1 to 2:1;
   0.1 to 5 wt. % of one or more cationic surfactants;
   0.1 to 10 wt. % of one or more fatty compounds chosen from fatty carbonates, glycerol fatty esters, and a mixture thereof; and
   0.1 to 10 wt. % of one or more fatty alcohols;
      wherein the composition is a solubilized, non-emulsified composition until applied to wet or damp hair, whereupon the composition forms a lamellar phase in situ; and all percentages by weight are based on the total weight of the composition.

2. The composition of claim 1, further comprising:
about 0.1 to about 50 wt. % of one or more glycols selected from ethylene glycol, butylene glycol, hexylene glycol, pentylene glycol, diethylene glycol, dipropylene glycol, 1,3 propanediol, and glycerin.

3. The composition of claim 1, wherein the composition further comprises:
about 0.1 to about 20 wt. % of one or more thickening agents.

4. The composition of claim 3, wherein the one or more thickening agents are selected from polyacrylate crosspolymers or crosslinked polyacrylate polymers, cationic acrylate copolymers, anionic acrylic or carboxylic acid polymers, polyacrylamide polymers, polysaccharides, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof.

5. The composition of claim 1, wherein the one or more cationic surfactants are selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, di stearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

6. The composition of claim 1 comprising one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof.

7. The composition of claim 1 comprising one or more fatty alcohols selected from cetearyl alcohol, stearyl alcohol, behenyl alcohol, cetyl alcohol, myristyl alcohol, isostearyl alcohol, lauryl alcohol, and a mixture thereof.

8. The composition of claim 1, comprising one or more glycerol fatty esters selected from caprylic/capric triglycerides, glyceryl oleate, glyceryl stearate, glyceryl isostearate, glyceryl laurate, and a mixture thereof.

9. The composition of claim 1, wherein the composition is essentially free of silicones.

10. A transparent and substantially anhydrous cosmetic composition comprising:
50 to about 90 wt. % of propylene glycol;
5 to 30 wt. % of ethanol;
wherein the weight ratio of the propylene glycol to ethanol (propylene glycol:ethanol) is from 20:1 to 2:1;
about 0.1 to about 5 wt. % one or more cationic surfactants;
about 0.1 to about 10 wt. % of one or more fatty esters chosen from fatty carbonate esters, glycerol fatty esters, and a mixture thereof;
about 0.1 to about 10 wt. % of one or more fatty alcohols selected from cetearyl alcohol, stearyl alcohol, behenyl alcohol, cetyl alcohol, myristyl alcohol, isostearyl alcohol, lauryl alcohol, and a mixture thereof;
wherein the composition is a solubilized, non-emulsified composition until applied to wet or damp hair, whereupon the composition forms a lamellar phase in situ; and
all percentages by weight are based on the total weight of the composition.

11. The composition of claim 10, further comprising:
about 0.1 to about 50 wt. % of one or more glycols selected from ethylene glycol, butylene glycol, hexylene glycol, pentylene glycol, 1,3-propanediol, diethylene glycol, dipropylene glycol, caprylyl glycol, glycerin, and a mixture thereof; and
optionally, about 0.1 to about 20 wt. % of one or more thickening agents.

12. The cosmetic composition of claim 10 comprising:
50 to about 90 wt. % of propylene glycol;
5 to 30 wt. % of ethanol;
about 0.1 to about 5 wt. % one or more cationic surfactants selected from cetrimonium chloride, behentrimonium chloride, behentrimonium methosulfate, stearamidopropyl dimethylamine, and a mixture thereof;
about 0.1 to about 10 wt. % of one or more fatty carbonates; and
about 0.1 to about 10 wt. % of one or more fatty alcohols selected from cetearyl alcohol, stearyl alcohol, behenyl alcohol, cetyl alcohol, myristyl alcohol, isostearyl alcohol, and a mixture thereof.

13. A method for treating hair comprising applying a transparent and substantially anhydrous cosmetic composition to wet or damp hair and forming a lamellar phase in situ, the transparent and substantially anhydrous cosmetic composition comprising:
50 to 90 wt. % of propylene glycol;
5 to 30 wt. % of one or more monoalcohols having from 2 to 6 carbon atoms;
wherein the weight ratio of the propylene glycol to the monoalcohol(s) (propylene glycol:monoalcohol(s)) is from 20:1 to 2:1;
about 0.1 to about 5 wt. % of one or more cationic surfactants;
0.1 to 10 wt. % of one or more fatty compounds chosen from fatty carbonates, glycerol fatty esters, and a mixture thereof; and
0.1 to 10 wt. % of one or more fatty alcohols;
wherein the composition is a solubilized, non-emulsified composition until applied to the wet or damp hair, whereupon the composition forms a lamellar phase in situ; and
all percentages by weight are based on the total weight of the composition.

14. The method of claim 13, wherein the composition is applied to the wet or damp hair by spraying.

15. The method of claim 13, further comprising cleansing the hair after application of the composition to the wet or damp hair, prior to styling the hair.

16. A method of claim 13, wherein treating the hair comprises:
conditioning the hair;
providing curl definition to the hair;
providing frizz control to the hair;
improving ease of comb ability and detangling;
protecting the hair from damage;
increasing the appearance of hair volume; and
imparting or improving shine on hair.

* * * * *